United States Patent [19]

Nichols et al.

[11] Patent Number: 5,783,700
[45] Date of Patent: Jul. 21, 1998

[54] QUINOLIC ACID DERIVATIVES

[76] Inventors: Alfred C. Nichols, 111 West Oak Hill Dr., Florence, Ala. 35633; K. Lemone Yielding, 511 Woodland Dr., Tuscumbia, Ala. 35674

[21] Appl. No.: 887,627

[22] Filed: Jul. 3, 1997

[51] Int. Cl.$^6$ .............................................. C07D 215/42
[52] U.S. Cl. .................................................. 546/162
[58] Field of Search .................................... 546/162

[56] References Cited

U.S. PATENT DOCUMENTS

| | | |
|---|---|---|
| 4,788,188 | 11/1988 | Vernieres et al. |
| 5,017,576 | 5/1991 | Dubroeucq et al. |
| 5,026,700 | 6/1991 | Harrison et al. |
| 5,208,707 | 7/1991 | Nichols et al. |
| 5,250,541 | 10/1993 | Moroni et al. |
| 5,252,584 | 10/1993 | Carling et al. |
| 5,270,309 | 12/1993 | Leeson . |
| 5,344,922 | 9/1994 | Nichols et al. |
| 5,348,962 | 9/1994 | Kulagowski et al. |
| 5,493,027 | 2/1996 | Nichols et al. |

OTHER PUBLICATIONS

Leeson et al., 4-Amido-2-carboxytetrahydroquinolines. Structure–Activity Relationships for Antagonism at the Glycide Site of the NMDA Receptor, J. Med. Chem., 35:1954–1968 (1992).

Carling et al., 2-Carboxytetrahydroquinolines. Conformational and Stereochemical Requirements for Antagonism of the Glycine Site on the NMDA Receptor, J. Med. Chem., 35:1954–1968 (1992).

Leeson et al., Kynurenic Acid Derivatives. Structure–Activity Relationships for Excitatory Amino Acid Antagonism and Identification of Potent and Selective Antagonists, J. Med. Chem., 34:1243–1252 (1991).

*Primary Examiner*—Patricia L. Morris
*Attorney, Agent, or Firm*—Ken Bush, Veal & Associates

[57] ABSTRACT

Coupled to the N-methyl-D-aspartate (NMDA) receptor complex is a strychnine-insensitive binding site for glycine. Pharmacological antagonism of glycine at this site may produce anticonvulsant activity. Twelve 4-urea-5,7-dichlorokynurenic acid derivatives were synthesized and subsequently screened in mice for anticonvulsant activity using MES, Met, and TTE tests, and a rotorod test was used to determine neurotoxicity. Seven of the derivatives had anticonvulsant activity in TTE testing at 100 mg/kg. One derivative had an $ED_{50}$ value of 134 mg/kg in TTE testing. Two derivatives had MES activity. Only one derivative was neurotoxic in the rotorod test. Compounds were screened at a 10 uM concentration for activity in displacing 5,7-dichlorokynurenic acid from synaptosomal membrane fragments. Nine of the twelve compounds synthesized and tested have demonstrated anticonvulsant activity. Thus, compounds of the present invention should be usable for the treatment of epilepsy, neurodegenerative diseases, and other syndromes involving inhibition or excessive stimulation of the NMDA receptor complex.

15 Claims, No Drawings

QUINOLIC ACID DERIVATIVES

FIELD OF THE INVENTION

The present invention relates to agents useful in modifying neuroexcitation through excitatory amino acid antagonists. More particularly, the present invention relates to agents which interact with the N-methyl-D-aspartate (NMDA) receptor complex.

BACKGROUND OF THE INVENTION

Excitatory amino acid neurotransmitter systems are important in memory and learning (Izumi et al.; Morris et al.). A specific set of excitatory receptors of particular interest are those that selectively bind N-methyl-D-aspartic acid (NMDA). Activation of this transmitter system is probably a necessary step in the early formation of certain types of memory (Collingridge et al.), yet over-stimulation of these receptors can be toxic and result in cell death (Rondouin et al.). There is an increasing body of evidence that excitatory amino acid neurotransmitter systems are progressively affected in the course of Alzheimer's disease (Greenamyre, et al.; Foster et al.; Penney et al.), and have been implicated in a number of central nervous system (CNS) disorders including epilepsy (Wong et al.), hypoxia/ischemia brain damage (Rothman), Huntington's disease (Young et al.), AIDS encephalopathy (Giulian et al.), and amyotrophic lateral sclerosis (Spencer et al.).

Epilepsy, for example, is a complex disease process which is still poorly understood. A cellular or biochemical etiology cannot usually be identified. Treatment is generally focused on seizure control, with hopes that the condition will ameliorate on its own. Unfortunately, drug therapy for seizures is subject to much individual variation. Thus, treatment is frequently by trial and error. Various combinations of drugs in various dosages are typically administered in an effort to provide some degree of seizure control without causing overt neurotoxicity. Unfortunately, some 20–40% of epileptic patients fail to experience satisfactory results with the drugs currently available (Goehring et al., 1990). Moreover, many of these drugs produce troublesome side effects when administered over the long time periods required in treatment, which frequently spans years or decades. The design of drugs which act only at sites of inappropriate neuronal excitation should minimize unfavorable side effects such as ataxia and sedation. To this end, we have sought to develop compounds that will selectively attenuate activity at specific subsets of excitatory neuroreceptors.

The NMDA-sensitive receptor sites comprise a subset of the excitatory neuroreceptors that are activated by L-glutamic acid. The NMDA neuroreceptors are linked to non-selective ion channels (Nowak et al., 1984), which are voltage dependent and permeable to calcium. The receptor complex also has a strychnine-insensitive binding site for glycine. For channel opening to occur, apparently both glutamate and glycine binding sites must be occupied (Johnson and Ascher, 1987). Consequently, antagonism of glycine binding inhibits NMDA responses (Kemp et al., 1988). Since glutamate functions as an excitatory neurotransmitter, it is not surprising that inhibitors of NMDA activity have anticonvulsant properties (Dingledine et al., 1990). The quinoline derivative 7-chlorokynurenic acid is a competitive inhibitor of glycine binding at the NMDA receptor, and this is thought to be the mechanism of its anticonvulsant activity (Wong et al., 1986; Singh et al., 1990).

There is evidence that NMDA receptors are responsible, at least in part, for the neurotoxicity seen in ischemia, and to excitatoxic cell death (Rondouin et al.). Excitatoxicity is the neuronal degeneration caused by exposure of central nervous system tissue to excitatory amino acids. It has been shown that non-competitive antagonists of NMDA receptors protect cortical and hippocampal cell cultures against glutamate neurotoxicity (Rondouin et al.). Calcium entry through the NMDA receptor channel is thought to be the mechanism by which glutamate released from nerve terminals can regulate long-term physiological events and, under pathological conditions, precipitate neurodegeneration. In addition, it has been recently reported that the glycine NMDA receptor is involved in the behavioral effects of cocaine (Morrow et al., 1995) and in ethanol activity in the CNS (Morris and Leslie, 1996). NMDA receptor antagonists have also been shown to possess analgesic (Dickenson and Aydar, 1991), anti-depressant (Trullas and Skolnick, 1990), and anxiolytic effects (Kehne et al., 1991). Compounds of the present invention may accordingly be useful in the management of pain, depression, and anxiety, and in the prevention or reduction of dependence on addictive agents such as narcotics.

It should be feasible to design and synthesize efficacious amino acid analogs as therapeutic agents for the NMDA receptor complex once binding characteristics are understood. However, it needs to be remembered that a simple agonist for the NMDA receptor could be neurotoxic, while an antagonist might potentiate memory loss. Research relating to the present application has been directed towards the glycine modulatory site on the NMDA receptor complex (Johnson et al.). Development of a strategy for pharmacological intervention at this site should lead to the production of drugs with mixed agonist-antagonist activities that could be clinically useful while having minimal side effects. Although potent glycine site ligands have been synthesized, in most cases these have had poor in vivo anticonvulsant activity (Rowley et al., 1993; Leeson et al., 1992). We have reported previously on several kynurenic acid derivatives that had anticonvulsant activity (Nichols and Yielding, 1993). These compounds also compete for [$^3$H]-glycine binding in synaptosomal assays. Leeson et al. (1992) showed that in another series of rigid ring glycine ligands, the 2-carboxytetrahydroquinolines, 4-urea derivatives were more potent glycine antagonist than either 4-amines or 4-amides. However, the 2-carboxytetrahydroquinoline derivatives had poor in vivo activity following intraperitoneal (ip) or intravenous (iv) administration (Leeson and Iversen, 1994).

In an effort to produce anticonvulsants with in vivo potency, we have synthesized a unique series of 4-urea-5, 7-dichlorokynurenic acid derivatives. These were evaluated for anticonvulsant activity in maximal electroshock (MES), subcutaneous pentylenetetrazole (Met), and threshold tonic extension (TTE) tests. They were also assayed for strychnine-insensitive glycine binding inhibition using a synaptosomal membrane preparation. One compound was also tested for phencyclidine (PCP) activity at the NMDA receptor, and for GABA-A effects.

SUMMARY OF THE PRESENT INVENTION

Coupled to the N-methyl-D-aspartate (NMDA) receptor complex is a strychnine-insensitive binding site for glycine. Pharmacological antagonism of glycine at this site may produce anticonvulsant activity. Twelve derivatives of 5,7-dichlorokynurenic acid were synthesized with an urea substituent at the 4-position. Various hydrophobic di-substitutions were made on the terminal nitrogen of the urea group. The lead compound in this series was 2-methyl carboxylate-5,7-dichloro-4-[[(diphenylamino)-carbonyl] aniino]-quinoline. Diethyl, dimethyl, dibutyl and 3-methoxydiphenyl amino derivatives were also produced. Both 2-carboxylic acid and 2-ester derivatives (ethyl and methyl) were synthesized. Each compound was evaluated for in vivo anticonvulsant activity using two or three different testing protocols, and an in vivo screening for neurotoxicity was also conducted.

Of this group, only two compounds did not show any in vivo activity. One compound, an N,N-diethylamino derivative, was the only analog which proved to be neurotoxic in the rotorod test. Two of the analogs had MES activity, both of which were 2-carboxylic acids. The other seven compounds all demonstrated TTE anticonvulsant activity at 100 mg/kg. TTE effects were seen in both acid and ester derivatives. Compounds with N,N-diethyl, dimethyl, dibutyl, and diphenyl substituents were active in TTE testing as was the 3-methoxy-diphenylamine derivative. An $ED_{50}$ (effective dose) value for TTE activity was generated for 2-methyl carboxylate-5,7-dichloro-4-[[(diphenylamino)-carbonyl]amino]-quinoline: 134 mg/kg (95% Conf Int: low-78.5, high-205.7; slope=1.9, S.E.=0.44). None of these derivatives were active in the Met test even at the 300 mg/kg dose.

Seven selected compounds were screened for [$^3$H]-5,7-dichlorokynurenic acid displacement at a single dose of 10 uM. The greatest displacement was seen in derivatives having 2-carboxylic acid. The least was seen in compounds having 2-ethyl esters. As a group, the methyl esters fell somewhat inbetween.

Dose-response displacement assays were conducted using 2-methyl carboxylate-5,7-dichloro-4-[[(diphenylamino)-carbonyl]amino]-quinoline and [$^3$H]-TCP (both with and without added glycine), and [$^3$H]-muscimol. Displacement of [$^3$H]-TCP binding was assayed in the presence of 10 uM L-glutamic acid and 3 uM glycine. This assay was conducted twice with triplicate samples and concentrations of test compound ranging from 1 uM to 5 nM. No significant effect on [$^3$H]-TCP binding was observed in this assay. Repetition of the TCP displacement experiment with L-glutamate but no added glycine gave similar results over a dose range of 5 uM to 10 nM. A synaptosomal competition binding assay was also conducted using 2-methyl carboxylate-5,7-dichloro-4-[[(diphenylamino)-carbonyl] amino]-quinoline and the ligand [$^3$H]-muscimol. The purpose of this experiment was to check for activity at the GABA-A receptor complex. No significant effects were observed. The compound 2-methyl carboxylate-5,7-dichloro4-[[(diphenylamino)-carbonyl]amino]-quinoline also tested negative for PCP activity at the NMDA receptor, and for GABA-A effects.

The quinoline and kynurenin derivatives of the present invention have affinity for the glycine binding site of the NMDA receptor. Compounds of the present invention should be usable for the treatment of epilepsy, neurodegenerative diseases, and other syndromes involving inhibition or excessive stimulation of the NMDA receptor complex, and for the prevention of ischemic/hypoxic damage to cerebral tissue.

DETAILED DESCRIPTION OF THE PREFERRED EMBODIMENT

Syntheses—All chemicals for synthetic procedures were obtained from Aldrich (Milwaukee, Wis.). The procedure of Harrison et al. (1990) was used to make both methyl and ethyl esters of 5,7-dichlorokynurenic acid. In accordance with this procedure, either dimethyl or diethyl acetylene dicarboxylate was refluxed with 3,5-dichloroaniline in absolute methanol, or ethanol, respectively. Following solvent removal by evaporation, the product was added to mineral oil at 250° C. to form the corresponding 2-ester of 5,7-dichlorokynurenic acid. Replacement of the 4-hydroxyl group with an amine was accomplished using 4-toluenesulphonyl isocyanate (Wright, 1984) refluxed with acetonitrile. The resulting tosylimino derivative was reacted first with triphosgene in anhydrous pyridine at room temperature and then with a secondary amine having the desired substitution groups attached thereto, also in anhydrous pyridine. Ammonia is substituted for the secondary amine if hydrogen is desired in substitution positions $R_1$ and $R_2$, described below. Detosylation of the resulting compound in cold sulfuric acid (approximately 0° C.) gave the 5,7-dichloro4-urea-2-quinoline methyl (or ethyl) carboxylate. Ester hydrolysis with lithium hydroxide was used to generate the 2-carboxylic acids.

Piperidine and piperazine derivatives were also synthesized from the tosylimino derivative. For these compounds, the 4-amino quinoline compound was detosylated and then reacted with a stoichiometric concentration of triphosgene in anhydrous pyridine. On completion of this reaction, a stoichiometric amount of the cyclic amine was added to form the corresponding 2-ethyl(or methyl)-carboxylate-5,7-dichloro4-[[(piperidino or piperazino)-carbonyl]amino]-quinoline.

Structures were verified using nuclear magnetic resonance (NMR) spectroscopy and elemental analysis. The structure of the present invention is illustrated as follows:

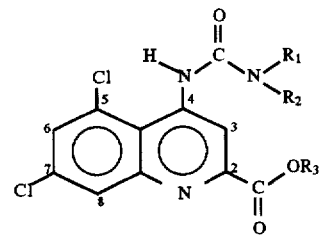

wherein positions $R_1$, $R_2$, and $R_3$ for the 12 compounds discussed herein have the substitution groups listed in Table 1.

TABLE 1

| Compound No. | $R_1$ Group | $R_2$ Group | $R_3$ Group |
|---|---|---|---|
| 1 | ethyl | ethyl | methyl |
| 2 | ethyl | ethyl | ethyl |
| 3 | ethyl | ethyl | hydrogen |
| 4 | methyl | methyl | ethyl |
| 5 | methyl | methyl | hydrogen |
| 6 | n-butyl | n-butyl | ethyl |
| 7 | n-butyl | n-butyl | hydrogen |
| 8 | phenyl | phenyl | ethyl |
| 9 | phenyl | phenyl | hydrogen |
| 10 | phenyl | phenyl | methyl |
| 11 | phenyl | 3-methoxyphenyl | ethyl |
| 12 | phenyl | 3-methoxyphenyl | hydrogen |

The substitution groups on the B-ring of the quinoline molecule are not limited to chlorine molecules or to sites 5 and 7, but rather, any of the halogens fluorine, chlorine, bromine, or iodine, or hydrogen, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms can be substituted into sites 5–8. To synthesize the foregoing, an aniline compound having the desired substitution groups is substituted for 3,5-dichloroaniline in the synthesis described above. These B-ring substitutions affect the solubility of the molecule and its ability to pass through the blood-brain barrier. Consequently, interchanging these B-ring substitution groups will only change the effective dose (ED) of the particular molecule and not the interaction of the A-ring with the NMDA receptor complex. Thus, a more accurate illustration of the structure defining the present invention is:

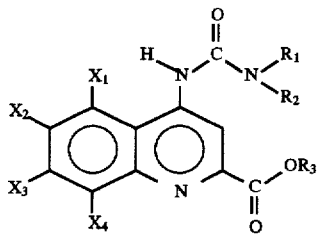

wherein positions $R_1$, $R_2$, and $R_3$ have the same substitution groups as those listed in Table 1; and $X_1$, $X_2$, $X_3$, and X4 are selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms.

Because of the results found with compounds 1–12, hydrogen or any branched or straight-chained alkyl group containing from 1 to 6 carbon atoms could be substituted at either the $R_1$ or $R_2$ sites and exhibit anticonvulsant activity. Furthermore, ring substitutions at the $R_1$ and $R_2$ sites may exhibit anticonvulsant activity. We have synthesized derivatives of 5,7-dichlorokynurenic acid having either a piperidine or piperazine substitution at the $R_1$ and $R_2$ sites, although we have not yet tested these compounds for anticonvulsant activity. The present invention having the piperidine substitution has the following structure:

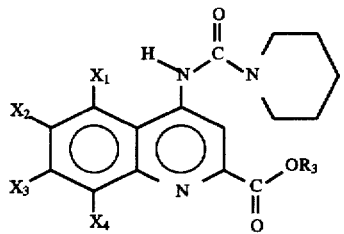

wherein position $R_3$ has the same substitution groups as that listed in Table 1; and $X_1$, $X_2$, $X_3$, and X4 are selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms. The present invention having the piperazine substitution has the following structure:

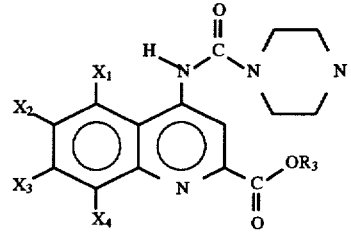

wherein position $R_3$ has the same substitution groups as that listed in Table 1; and $X_1$, $X_2$, $X_3$, and $X_4$ are selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms.

The present invention also includes any prodrugs or pharmaceutically acceptable addition salts of the molecules described herein. As used in the present application, the term "prodrug" applies to any inactive precursors of the compounds described herein which are subsequently activated in vivo, and "pharmaceutically acceptable addition salt" applies to any nontoxic organic or inorganic addition salt of the basic compounds described herein. These salts may be acid addition salts or basic addition salts. Typical inorganic addition salts include those resulting from hydrochloric, hydrobromic, sulfuric, phosphoric and acid methyl salts such as sodium monohydrogen, orthophosphate and potassium hydrogen sulfate. Illustrative organic acids which form acceptable salts include mono-, di- and tricarboxyllic acids, for example, acetic, glycolic, lactic, pyruvic, malonic, succinic, glutaric, fumaric, malic, tartaric, citric, ascorbic, maleic, hydroxymaleic, benzoic, hyroxybenzoic, phenylacetic, and so forth. Pharmaceutically acceptable basic addition salts applied to any organic or inorganic basic addition salts including those resulting from alkali metal or alkali-earth metal hydroxides, ammonia, aliphatic, alicyclic or aromatic organic amines.

Biological Testing—Compounds were screened for anticonvulsant activity in male Carworth Farms no. 1 mice. The maximal electroshock (MES), subcutaneous Metrazol (pentylenetetrazole) (Met), and threshold tonic extension (TTE) tests were used to evaluate compounds for anticonvulsive activity. A rotorod protocol was used to determine neurotoxicity. Solutions for injection were prepared in 30% polyethylene glycol 400. Except for the TTE tests, animals were dosed ip at two different time periods: either 30 min. or 4 hr prior to testing. At each time period, three groups of four mice were tested at the following dose levels: 30, 100, and 300 mg/kg. This treatment protocol was followed for MES, Met, and rotorod testing.

Maximal electroshock (MES) induced seizures were elicited with a 60 cycle alternating current of 50 mA intensity (five to seven times the intensity necessary to evoke minimal electroshock threshold seizures). Current was delivered via corneal electrodes for 0.2 sec. A drop of 0.9% saline was instilled in the eye prior to application of the electrodes. Abolition of the hindlimb tonic extension component of the seizure was defined as protection.

In the subcutaneous Metrazol induced seizure threshold (Met) test, 85 mg/kg pentylenetetrazole was administered as a 0.5% solution in the posterior midine. Protection was defined as a failure to observe a single episode of clonic spasms of at least 5 sec. duration during the 30 min. period following administration of the convulsive agent.

The threshold tonic extension (TTE) test is similar to the MES screen but uses a lower level of electrical current (Piredda et al., 1985). The lower current makes the test more sensitive but less discriminate than the MES screen. Twenty mice were pretreated ip with 100 mg/kg of the test compound. At time intervals of ¼, ½, 1, 2, and 4 hr post treatment, 4 mice were challenged with 12.5 mA of electrical current for 0.2 sec. via corneal electrodes. This current produces a TTE seizure in untreated animals. Protection was defined as an absence of seizures. Additional TTE testing was conducted on compound 10 to determine the $ED_{50}$ value for the observed protective effect. In this case, 6 groups containing either 8 or 16 animals were injected ip and tested two hours following treatment. Each group received a specified dose ranging from 20–500 mg/kg. An $ED_{50}$ value was determined from a log dose-response plot of the resulting data.

Animals were tested for drug induced neurological deficit using a rotorod. Either 30 min. or 4 hr after treatment, the animal was placed on a 1-inch diameter knurled plastic rod rotating at 6 rpm. Neurological deficit was defined as the failure of the animal to remain on the rod for 1 min.

Binding Studies—The procedure of Baron et al. (1991) was used to assay for the inhibition of specific binding at the glycine binding site on the NMDA receptor. The labeled ligand used in this assay was [$^3$H]-5,7-dichlorokynurenic acid (15.8 Ci/mmol) from DuPont-New England Nuclear (Boston, Mass.). This ligand is reported to have identical specificity and higher affinity (Kd=29 nM) than [$^3$]-glycine for the binding site (Canton et al., 1992). Inhibition of specific binding was determined for selected compounds at a concentration of 10 uM using "buffy coat" membrane fragments (Jones et al., 1989). Membranes were prepared from rat cerebral cortex and assays were conducted in 50 mM HEPES-KOH buffer (Sigma, St. Louis, Mo.) at pH 7.4. Membranes were incubated in a final volume of 1 mL containing 10 nM [$^3$H]-5,7-dichlorokynurenic acid. Incubation was continued for 15 min. at 4° C. Nonspecific binding was determined in the presence of 1 mM glycine and subtracted. Binding was terminated by centrifugation at 48,000×g for 10 min. Each of the resultant pellets was washed rapidly with 1 mL ice water and solubilized with 1 mL of a tissue solubilizer (Solvable, DuPont NEN). The solubilized samples were each dissolved in 10 mL 3a70B Complete Counting Cocktail (RPI, Mount Prospect, Ill.). Membrane bound radioactivity was determined using a Beckman LS-5000TD liquid scintillation counter. This screening procedure was conducted in triplicate in three separate tests. Results are presented as percent of control (±SEM, standard error of the mean).

Compound 10 was also screened for activity at the NMDA-associated PCP binding site, and, additionally, for activity at the GABA-A neuroreceptor. To determine possible effects on PCP binding, N-(1-(2-thienyl)cyclohexyl)-3,4-[$^3$H]-piperidine ("[$^3$H]-TCP") binding was assayed using the technique of Johnson et al. (1988). TCP is the thienyl derivative of PCP. Binding of [$^3$H]-TCP to the NMDA receptor complex can be modulated by glycine agonists and antagonists (Benavides et al., 1988). DuPont-New England Nuclear was the source for [$^3$H]-TCP (44.5 Ci/mmol). Membranes were prepared as described above. Assays were conducted in 5 mM Tris-acetate (pH 7.4) buffer containing 10 uM L-glutamic acid and 3 uM glycine. Each sample had a final volume of 1 mL and contained 2 nM [$^3$H]-TCP. Nonspecific binding was determined in the presence of 30 uM PCP and subtracted. Samples were incubated at 24° C. for 1 hr. Binding was terminated using a Brandel M-24C cell harvester employing rapid filtration through GF/C glass filters presoaked in 0.1%(v/v)polyethylenimine. Filters were washed rapidly with two 1 mL aliquots of ice-cold water. Samples were run in triplicate at six different drug concentrations ranging from 1 uM to 5 nM. The experiment was repeated with buffer containing 0.1 mM L-glu and no added glycine. Two separate assays were conducted for each experiment.

Compound 10 was screened for activity at the GABA-A neuroreceptor complex using [$^3$H]-muscimol (20.0 Ci/mmol), also from DuPont-New England Nuclear. The filtration method reported by Williams and Risley (1979) was used for this assay. Membranes were initially prepared as described previously and frozen at −20° C. in distilled water for 24 hr. After thawing, membranes were resuspended in 50 mM Tris-acetate buffer (pH 7.0) which contained 0.1% (v/v) saponin (Sigma). The tissue was centrifuged at 48,000×g for 20 min. and the resulting pellet was resuspended in 30 volumes of 50 mM Tris-acetate buffer (pH 7.0) containing 100 mM KCl. The tissue was again centrifuged at 48,000×g for 20 min. After decanting the supernatant, the pellet was covered with fresh KCl containing Tris-acetate buffer and frozen for 24 hr.

On the day of the assay, the tissue was thawed and resuspended in 30 volumes of 50 mM Trisacetate (pH 7.0) with 100 mM KCl and centrifuged at 48,000×g for 20 min. This washing procedure was repeated twice. The final pellet was resuspended in 32 mL buffer. Membranes were incubated in a final volume of 1 mL with 5 nM [$^3$H]-muscimol at 4° C. for 30 min. Samples were run in triplicate employing six different concentrations of compound 10 ranging from 10 uM to 10 nM. The assay was performed in duplicate. Each sample, including controls, contained 1.0% dimethyl sulfoxide (DMSO) to insure solubilization of the test compound. Nonspecific binding was determined in the presence of 200 uM gamma-aminobutyric acid (GABA) and subtracted. Binding was terminated using a Brandel M-24C cell harvester employing rapid filtration through GF/C glass fiber filters presoaked in 0.1% (v/v) polyethylenimine. Filters were washed with 1 mL cold water. Radioactivity bound to the filters was determined by scintillation counting.

Results—Twelve derivatives of 5,7-dichlorokynurenic acid were synthesized with an urea substituent at the 4-position. Various hydrophobic di-substitutions were made on the terminal nitrogen of the urea group. The lead compound in this series, compound 10, was 2-methyl carboxylate-5,7-dichloro-4-[[(diphenylamino)-carbonyl] amino]-quinoline. Diethyl, dimethyl, dibutyl and 3-methoxydiphenyl amino derivatives were also produced. Both 2-carboxylic acid and 2-ester derivatives (ethyl and methyl) were synthesized. Each compound was evaluated for in vivo anticonvulsant activity using two or three different testing protocols. An in vivo screening for neurotoxicity was also conducted. The results of the tests are summarized in Table 2.

Of this group, only compounds 1 and 4 showed no in vivo activity, although the TTE test was not performed on compound 1. Compound 3, an N,N-diethylamino derivative, was the only analog which proved to be neurotoxic in the rotorod test. Two of the analogs had MES activity: compound 5 at 300 mg/kg and compound 12 at 100 mg/kg. Both of these were 2-carboxylic acids. The other seven compounds all demonstrated TTE anticonvulsant activity at 100 mg/kg.

TTE effects were seen in both acid and ester derivatives. Compounds with N,N-diethyl, dimethyl, dibutyl, and diphenyl substituents were active in testing as was the 3-methoxydiphenylamine derivative 11. An $ED_{50}$ value for TTE activity was generated for compound 10: 134 mg/kg (95% Conf Int: low-78.5, high-205.7; slope=1.9, S.E.=0.44). None of these derivatives were active in the Met test even at the 300 mg/kg dose.

TABLE 2

Effective or [maximum ineffective] intraperitoneal dose (mg/kg)

| Compound No. | MES | Met | TTE | Rotorod |
|---|---|---|---|---|
| 1 | [300] | [300] | nt | [300] |
| 2 | [300] | [300] | 100 | [300] |
| 3 | [300] | [300] | [100] | 300 |
| 4 | [300] | [300] | [100] | [300] |
| 5 | 300 | [300] | nt | [300] |
| 6 | [300] | [300] | 100 | [300] |
| 7 | [300] | [300] | 100 | [300] |
| 8 | [300] | [300] | 100 | [300] |
| 9 | [300] | [300] | 100 | [300] |
| 10 | [300] | [300] | 100 | [300] |
| 11 | [300] | [300] | 100 | [300] |
| 12 | 100 | [300] | nt | [300] | nt = not tested

Seven selected compounds were screened for [$^3$H]-5,7-dichlorokynurenic acid displacement at a single dose of 10 uM. These results are reported in Table 3 as percent of control (±SEM). The greatest desplacement was seen in derivatives having the 2-carboxylic acid. The least was seen in compounds having 2-ethyl esters. As a group, the methyl esters fell somewhat in-between. Dose-response curves with [$^3$H]-5,7-dichlorokynurenic acid have not been completed due to technical problems with assay at low drug concentrations.

TABLE 3

Inhibition of [$^3$H]-5,7-Dichlorokynurenic Acid Binding by 10 uM Concentrations of Test Compounds

| Compound No. | % of Control* |
|---|---|
| 1 | 58 ± 8 |
| 4 | 57 ± 1 |
| 6 | 76 ± 6 |
| 7 | 20 ± 11 |
| 8 | 77 ± 7 |
| 9 | 25 ± 5 |
| 10 | 42 ± 7 |

*Each value is the mean ± SEM of three determinations, each performed in triplicate.

Dose-response displacement assays were conducted using compound 10 and [$^3$H]-TCP (both with and without added glycine), and [$^3$H]-muscimol. Displacement of [$^3$M]-TCP binding was assayed in the presence of 10 uM L-glutamic acid and 3 uM glycine. This assay was conducted twice with triplicate samples and concentrations of test compound ranging from 1 uM to 5 nM. No significant effect on [$^3$H]-TCP binding was observed in this assay. Repetition of the TCP displacement experiment with L-glu but no added glycine gave similar results over a dose range of 5 uM to 10 nM. A synaptosomal competition binding assay was also conducted using compound 10 and the ligand [$^3$H]-muscimol. The purpose of this experiment was to check for activity at the GABA-A receptor complex. No significant effects were observed.

Discussion—Of the twelve 4-urea-5,7-dichlorokynurenic acid derivatives that were synthesized, nine had anticonvulsant activity. Seven were active in TTE testing at 100 mg/kg, and two others, compounds 5 and 12, demonstrated activity in MES testing. None of the derivatives were active in the Met test, even at a dose of 300 mg/kg. Only one, compound 3, showed neurotoxicity as evidenced by the rotorod test, and this was observed only at a dose of 300 mg/kg. When the lipophilic dibutyl and diphenyl groups were placed on the terminal urea nitrogen, TTE activity was observed with both ester and carboxylic acid derivatives. Compound 10, the lead compound in the series, had an $ED_{50}$ of 134 mg/kg in TTE testing. Placement of lipophilic diphenyl and dibutyl groups on the urea amine may improve drug penetration across the blood-brain barrier. Only two derivatives, 1 and 4, showed no CNS activity. As these compounds had the less lipophilic diethyl and dimethyl groups on the terminal urea nitrogen, they may not have reached therapeutic concentrations in the CNS. It has been proposed that the low anticonvulsant activity seen with the kynurenate class of glycine antagonists is due to poor penetration of the blood-brain barrier (Rowley et al., 1993).

Data from the Table 3 demonstrate that these derivatives can antagonize NMDA-associated glycine binding. At a concentration of 10 uM all of those compounds tested demonstrated some degree of displacement of [$^3$H]-5,7-dichlorokynurenic acid in synaptosomal assays. At the test concentration, compound 10 produced a displacement which was 42% of control. Compounds 7 and 9, both of which are 2-carboxylic acids with either dibutyl or diphenyl hydrophobic groups on the urea amine, were even better, with displacements in the range of 20–30% of control. Derivatives with ethyl esters at the 2-position were not as active in this assay. The observation that compounds 1 and 4 were active in the glycine assay, but did not have any in vivo effects, supports the contention that they do not readily enter the CNS. The data summarized in Table 3 indicate that this class of compounds is potentially useful in the treatment or prevention of a multitude of neurodegenerative disorders.

Glycine antagonists such as 7-chlorokynurenic acid have been shown to decrease binding of phencyclidine-like compounds which bind to a recognition site presumed to be located within the ion channel of the receptor complex (Tacconi et al., 1993). However, at a concentration of 1 uM, compound 10 demonstrated no significant effect on TCP binding either with or without added glycine. Compound 10 was also tested in a [$^3$H]-muscimol competition assay to determine if the derivative affected GABA binding. No significant difference from control was detected in this protocol, even at a high of dose of 10 uM.

Based on the results of the anticonvulsant testing, the 2-carboxy4-urea quinoline derivatives are able to cross the blood-brain barrier and reach therapeutic levels in the CNS. Unfortunately, the mechanism of action is still unclear. Results from in vitro assays indicate that the urea quinolines can interact at the NMDA glycine binding site. However, the lack of effect on TCP binding at a 1 uM concentration, suggests that they are not particularly potent glycine antagonists. In a similar type of assay using [$^3$H]-MK 801, 7-chlorokynurenic acid had an $IC_{50}$ (inhibition concentration) in the range of 30–40 uM (depending on brain region), and showed little effect at 1 uM (Tacconi et al., 1993). It could be that micromolar receptor affinity is sufficient for anticonvulsant activity, or the in vivo protective effect results from another CNS interaction. It remains to be determined if these compounds also interact with sodium channels or other sites involved in neuroexcitation. If another receptor is involved in the in vivo anticonvulsant activity, it does not appear to be the GABA-A receptor, as compound 10 had no effect on [$^3$H]-muscimol binding. The fact that nine of the twelve compounds have demonstrated in vivo anticonvulsant activity offers promise for effective therapeutic agents from this class of chemicals.

The following citations are incorporated herein by reference:

REFERENCES

Baron, et al. (1990) Activity of 5,7-dichlorokynurenic acid, a potent antagonist at the N-methyl-D-aspartate receptor-associated glycine binding site. *Mol. PharmacoL* 38, 554–561.

Canton, T., et al. (1992) A rapid filtration assay for the glycine binding site on the NMDA receptor in Rat Cortical membranes using [$^3$H] Dichlorokynurenic Acid. *J Pharm. Pharmacol.* 44, 812–816.

Collingridge, et al. (1987) *TINS.* 10, 288–293.

Cortes, et al. (1985) Effect of structural modification of the hydantoin ring on anticonvulsant activity. *J Med. Chem.* 28, 601–606.

Dickenson, A. H. and Aydar, E. (1991) Antagonism at the glycine site on the NMDA receptor reduces spinal nociception in the rat. *Neurosci. Lett.* 121, 263–266.

Dingledine, et al. (1990) Excitatory amino acid receptors in epilepsy. *Trends Pharmacol. Sci.* 11, 334–338.

Foster, et al. (1992) Kynurenic acid analogues with improved affinity and selectivity for the glycine site on the N-methyl-D-aspartate receptor from rat brain. *Mol. Pharmacol* 41, 914–922.

Foster, (1990) *Adv. Neurol.* 51, 97–102.

Giulian, et al. (1990) *Science,* 250, 1593–1596.

Goehring, et al. (1990) Synthesis and anticonvulsant activity of 2-benzylglutarimides. *J. Med. Chem* 33, 926–931.

Greenamyre, et al. (1989) *NeurobioL Aging* 10, 593–602.

Harrison, et al. (1990) 4-[(Carboxymethyl)oxy]- and 4-[(carboxymethyl)amino]-5,7-dichloroquinoline-2-carboxylic acid: new antagonists of the strychnine-insensitive glycine binding site on the N-methyl-D-aspartate receptor complex. *J Med. Chem.* 33, 3130–3132.

Huettner (1989) Indole-2-carboxylic acid: a competitive antagonist of potentiation by glycine at the NMDA receptor. *Science* 24, 1611–1613.

Huettner (1991) Competitive antagonism of glycine at the N-methyl-D-aspartate receptor. *Biochem. Pharmacol.* 41, 9–16.

Izumi, et al. (1987) *Neurosci. Lett.* 83, 201–206.

Johnson, et al. (1988), N-Methyl-D-Aspartate Enhanced $^3$H-TCP Binding to Rat Cortical Membranes: Effects of divalent cations and glycine. *Sigma and Phencyclidine-like Compounds as Molecular Probes in Biology,* NPP Books, Ann Arbor, pp. 259–268.

Johnson, et al. (1987) Glycine potentiates the NMDA response in cultured mouse brain neurons. *Nature* 325, 529–531.

Jones, et al (1989) Characterization of the binding of radioligands to the N-methyl-D-aspartate, phencyclidine, and glycine receptors in buffy coat membranes. *J. Pharmacol Methods* 21, 161–168.

Kehne, et al. (1991) NMDA receptor complex antagonists have potential anxiolytic effects as measured with separation-induced ultrasonic vocalizations. *Eur. J. Pharmacol.* 193, 283–292.

Kemp, et al. (1988) 7-Chlorokynurenic acid is a selective antagonist at the glycine modulatory site of the N-methyl-D-aspartate receptor complex. *Proc. Natl. Acad. Sci. USA* 85, 6547–6550.

Kleckner, et al. (1989) Selectivity of quinoxalines and kynurenines as antagonists of the glycine site on N-methyl-D-aspartate receptors. *Mol Pharmacol.* 36, 430–436.

Leeson, et al. (1992) 4-Amido-2-carboxytetrahydroquinolines: Structure activity relationships for antagonism at the glycine site of the NMDA receptor. *J. Med. Chem.* 35, 1954–1968.

Leeson, et al. (1994) The Glycine Site on the NMDA Receptor: Structure-Activity Relationships and Therapeutic Potential. *J. Med Chem.* 37, 4053–4067.

McBain, et al (1989) Structural requirements for activation of the glycine co-agonist site of N-methyl-D-aspartate receptors expressed in Xenopus oocytes. *Mol Pharmacol.* 36, 556–565.

Morris, et al. (1986) *Nature* 319, 774–776.

Morris et al. (1996) Glutamate and cysteinylglycine effects on NMDA receptors: inhibition of ethanol. *Alcohol* 13, 157–162.

Morrow et al. (1995) R-(+)-HA-966, an antagonist for the glycine/NMDA receptor, prevents locomotor sensitization to repeated cocaine exposures. *Brain Res.* 673, 165–169.

Nichols, A. C. and Yielding, K. L. (1993) Anticonvulsant activity of antagonists for the NMDA-associated glycine binding site. *Mol. Chem. Neuropath.* 19, 269–282.

Nowak, et al. (1984) Magnesium gates glutamate-activated channels in mouse central neurones. *Nature* 307, 462–465.

Penney, et al. (1990) *J. Neurology, Neurosurgery and Psychiatry* 53, 314–320.

Piredda, et al. (1985) Effect of stimulus intensity on the profile of anticonvulsant activity of phenytoin, ethosuximide, and valproate. *J. Pharmacol Exp. Ther.* 232, 741–745.

Porter, et al. (1984) Anti-epileptic drug development program. *Cleve. Clin. Q.* 51, 293–305.

Rogawski, et al (1990) Anti-epileptic drugs: pharmacological mechanisms and clinical efficacy with consideration of promising developmental stage compounds. *Pharmacol. Rev.* 42, 223–286.

Rondouin, et al. (1988) *Neurosci. Left.* 91, 199–202.

Rothman, (1984) *J. Neurosci.* 4, 1884–1891.

Rowley, et al. (1993) 3-Acyl-4-hydroxyquinolin-2(1H)-ones: Systemically active anticonvulsants acting by antagonism at the glycine site of the N-methyl-D-aspartate receptor complex. *J. Med. Chem.* 36, 3386–3396.

Singh, et al. (1990) Modulation of seizure susceptibility in the mouse by the strychnine-insensitive glycine recognition site of the NMDA receptor/ionophore complex *Br. J. Pharmacol.* 99, 285–288.

Snell, (1990) The allosteric interactions between the N-methyl-D-aspartate (NMDA) and glycine sites of the NMDA receptor/ionophore complex. A Dissertation. The University of Texas Medical Branch, Galveston, Tex.

Snell, et al (1986) Characterization of the inhibition of excitatory amino acid-induced neurotransmitter release in the rat striatum by phencyclidine-like drugs. *J. Pharmacol Exp. Ther.* 238, 938–946.

Spencer, et al. (1987) *Science* 237, 517–522.

Stone, et al. (1981) Quinolinic acid: a potent endogenous excitant at amino acid receptors in CNS. *Eur. J. Pharmacol.* 72, 411–412.

Surrey, et al. (1946) Some 7-substituted 4-aminoquinoline derivatives. *J. Am. Chem. Soc.* 68, 113–116.

Swinyard, et al. (1985) Anti-epileptic drugs: detection, quantification, and evaluation. *Federation Proc.* 44, 2629–2633.

Tacconi, et al. (1993) Inhibition of [$^3$H]-(+)-MK 801 binding to rat brain sections by CPP and 7-chlorokynurenic acid: an autoradiographic analysis. *Br. J. Pharmacol.* 108, 577–582.

Trullas, R. and Skolnick, P. (1990) Functional antagonists at the NMDA receptor complex exhibit antidepressant actions. *Eur. J. Pharmacol.* 185, 1–10.

Tucker, et al. (1951) Apparent ionization exponents of 4-hydroxyquinoline, 4-methoxyquinoline and N-methyl-4-quinoline: evaluation of lactam-lactam tautomerism. *J. Am Chem. Soc.* 73, 1923–1928.

Vida, et al. (1977) *Anticonvulsants*, pp. 176–182, Academic Press, New York, NY.

Watkins, et al. (1990) Structure-activity relationships in the development of excitatory amino acid receptor agonists and competitive antagonists. *Trends Pharmacol Sci.* 11, 25–33.

White, et al. (1989) Glycine binding to rat cortex and spinal cord: binding characteristics and pharmacology reveal distinct populations of sites. *J. Neurochem.* 53, 503–512.

Wong, et al. (1986) The anticonvulsant MK-801 is a potent N-methyl-D-aspartate antagonist. *Proc. Natl. Acad. Sci. USA* 83, 7104–7108.

Wright, (1984) A simple one-pot conversion of alkyl 4-oxo-1,4-dihydroquinoline-2-carboxylates to 4-aminoquinoline-2-carboxylates using reactive isocyanates. *Synthesis*, 1058–1061.

Young, et al. (1988) *Science* 241, 981–983.

It is to be understood that the form of the invention described is a preferred embodiment thereof and that various changes and modifications may be made therein without departing from the spirit of the invention or scope as defined in the following claims.

Having set forth the nature of the invention, what is claimed is:

1. A compound of the formula:

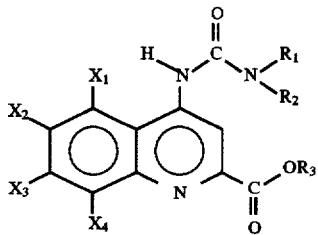

wherein:

$R_1$, is selected from the group consisting of hydrogen, ethyl, methyl, n-butyl, or phenyl;

$R_2$ is selected from the group consisting of hydrogen, ethyl, methyl, n-butyl, phenyl, or 3-methoxyphenyl;

$R_3$ is selected from the group consisting of ethyl, methyl, or hydrogen;

$X_1$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms;

$X_2$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms;

$X_3$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms; and $X_4$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms.

2. A compound according to claim 1, wherein:

$R_1$ is ethyl;

$R_2$ is ethyl; and $R_3$ is methyl.

3. A compound according to claim 1, wherein:

$R_1$ is ethyl;

$R_2$ is ethyl; and $R_3$ is ethyl.

4. A compound according to claim 1, wherein:

$R_1$ is ethyl;

$R_2$ is ethyl; and $R_3$ is hydrogen.

5. A compound according to claim 1, wherein:

$R_1$ is methyl;

$R_2$ is methyl; and $R_3$ is ethyl.

6. A compound according to claim 1, wherein:

$R_1$ is methyl;

$R_2$ is methyl; and $R_3$ is hydrogen.

7. A compound according to claim 1, wherein:

$R_1$ is n-butyl;

$R_2$ is n-butyl; and $R_3$ is ethyl.

8. A compound according to claim 1, wherein:

$R_1$ is n-butyl;

$R_2$ is n-butyl; and $R_3$ is hydrogen.

9. A compound according to claim 1, wherein:

$R_1$ is phenyl;

$R_2$ is phenyl; and $R_3$ is ethyl.

10. A compound according to claim 1, wherein:

$R_1$ is phenyl;

$R_2$ is phenyl; and $R_3$ is hydrogen.

11. A compound according to claim 1, wherein:

$R_1$ is phenyl;

$R_2$ is phenyl; and $R_3$ is methyl.

12. A compound according to claim 1, wherein:

$R_1$ is phenyl;

$R_2$ is 3-methoxyphenyl; and $R_3$ is ethyl.

13. A compound according to claim 1, wherein:

$R_1$ is phenyl; $R_2$ is methoxyphenyl; and $R_3$ is hydrogen.

14. A compound according to claim 1, wherein:

$X_1$ is chlorine;

$X_2$ is hydrogen;

$X_3$ is chlorine; and

X4 is hydrogen.

15. A compound of the formula:

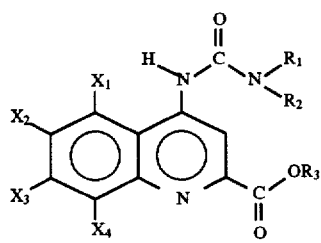

wherein:

- $R_1$ is selected from the group consisting of hydrogen or any branched or straight-chained alkyl groups containing from 1 to 6 carbon atoms;

- $R_2$ is selected from the group consisting of hydrogen or any branched or straight-chained alkyl groups containing from 1 to 6 carbon atoms;

- $R_3$ is selected from the group consisting of ethyl, methyl, or hydrogen;

- $X_1$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms;

- $X_2$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms;

- $X_3$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms; and

- $X_4$ is selected from the group consisting of hydrogen, fluoro, chloro, bromo, iodo, nitro, cyano, fluoromethyl, any branched or straight-chained alkyl group containing from 1 to 4 carbon atoms, any branched or straight-chained alkoxy group containing from 1 to 4 carbon atoms, any branched or straight-chained alkoxy carbonyl group containing from 1 to 4 carbon atoms, or any branched or straight-chained acyl group containing from 1 to 4 carbon atoms.

* * * * *

Adverse Decisions in Interference

Patent No. 5,783,700, Alfred C. Nichols, K. Lemone Yielding, QUINOLIC ACID DERIVATIVES, Interference No. 104,522, final judgment adverse to the patentees rendered. July 3, 2003, as to claims 1-15.
*(Official Gazette March 28, 2006)*